(12) United States Patent
Kropf et al.

(10) Patent No.: US 9,217,124 B2
(45) Date of Patent: Dec. 22, 2015

(54) WASHING OR CLEANING AGENT COMPRISING A HYDROGEL FORMER

(71) Applicant: Henkel AG & Co. KGaA, Duesseldorf (DE)

(72) Inventors: Christian Kropf, Hilden (DE); Matthias Sunder, Duesseldorf (DE); Peter Schmiedel, Duesseldorf (DE); Ulrich Pegelow, Duesseldorf (DE); Joerg C. Tiller, Herdecke (DE); Marco Mueller, Emmendingen (DE); Kaoru Tachikawa, Urdorf (CH); Yvonne Willemsen, Korschenbroich (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/243,980

(22) Filed: Apr. 3, 2014

(65) Prior Publication Data

US 2014/0303063 A1 Oct. 9, 2014

Related U.S. Application Data

(63) Continuation of application No. PCT/EP2012/066644, filed on Aug. 28, 2012.

(30) Foreign Application Priority Data

Oct. 4, 2011 (DE) .................. 10 2011 083 942

(51) Int. Cl.

| C11D 3/26 | (2006.01) |
|---|---|
| C11D 3/32 | (2006.01) |
| C11D 7/32 | (2006.01) |
| B08B 3/04 | (2006.01) |
| C11D 3/33 | (2006.01) |
| C11D 3/20 | (2006.01) |
| C11D 17/00 | (2006.01) |
| C07C 235/74 | (2006.01) |

(52) U.S. Cl.
CPC ............... *C11D 3/33* (2013.01); *C07C 235/74* (2013.01); *C11D 3/2068* (2013.01); *C11D 3/2093* (2013.01); *C11D 3/32* (2013.01); *C11D 17/003* (2013.01)

(58) Field of Classification Search
CPC ............. C11D 3/26; C11D 3/32; C11D 7/32; C11D 7/3263; B08B 3/04

USPC ......... 510/220, 230, 237, 475, 480, 499, 502; 134/25.2, 25.3, 39, 42
See application file for complete search history.

(56) References Cited

U.S. PATENT DOCUMENTS

| 6,576,679 B2 | 6/2003 | Kimizuka et al. |
| 2011/0220537 A1* | 9/2011 | Fernandez-Prieto et al. .................. 206/524.7 |

FOREIGN PATENT DOCUMENTS

| DE | 19933404 A1 | 1/2001 |
| EP | 1318191 A1 | 6/2003 |
| EP | 1553109 A1 | 7/2005 |
| EP | 2365052 A1 | 9/2011 |
| WO | 03/097587 A2 | 11/2003 |

OTHER PUBLICATIONS

PCT International Search Report (PCT/EP2012/066644) dated Dec. 12, 2012.
Estroff et al., "Water Gelation by Small Organic Molecules", Chemical Reviews, American Chemical Society, vol. 104, No. 3, pp. 1201-1217, 2004.
Loos et al., "Design and Application of Self-Assembled Low Moleculare Weight Hydrogels", European Journal of Organic Chemistry, No. 17, pp. 3615-3631, 2005.

* cited by examiner

*Primary Examiner* — Brian P Mruk
(74) *Attorney, Agent, or Firm* — Thomas G. Krivulka

(57) ABSTRACT

The invention relates to a washing or cleaning agent, wherein use thereof generates hydrogel layers surfaces, comprising a hydrogel former having a molecular weight less than 3500 g/Mol, wherein the hydrogel former is water-soluble at concentrations below the minimum gel formation concentration, wherein the minimum gel formation concentration is the concentration at which a yield point of at least 0.05 Pa is formed in a binary solution of water and hydrogel former at T=25° C., and wherein said minimum gel formation concentration lies below 2 wt % of hydrogel former, relative to the system consisting of water and hydrogel former. The washing or cleaning agents according to the invention enable the hydrophiliation of surfaces, and the specific and retarded releasing of active substances embedded in the hydrogel layers, such as aromatic substances or antimicrobial active substances, for example.

8 Claims, No Drawings

WASHING OR CLEANING AGENT COMPRISING A HYDROGEL FORMER

FIELD OF THE INVENTION

The present invention generally relates to washing or cleaning agents, and more particularly relates to washing or cleaning agents that comprise hydrogelators.

BACKGROUND OF THE INVENTION

Hydrogels are generally described in the prior art as water-containing gels based on hydrophilic, but water-insoluble polymers, which exist as three-dimensional networks. These networks swell up in water and to a large extent retain their shape. The formation of the network results from the addition of polymeric hydrogelators mainly through chemical linking of the individual polymer chains. Exemplary water-insoluble polymers that are added as the hydrogelator are based e.g. on poly(meth)acrylic acids, poly(meth)acrylates, polyvinyl pyrrolidone, polyvinyl alcohol or pectin.

The production of hydrogels by adding polymeric hydrogelators to surfaces in order to modify their properties is known. In this regard thicker layers can also be produced with methods such as the layer-by layer technique. However, the layer-by-layer technique requires the use of at least two different polymers and a multi-step process to produce the layers. The costs associated with this are felt to be disadvantageous.

When water-insoluble polymers are added as the hydrogelator, the residue of the polymer when the hydrogel layers are dissolved, e.g. by high dilution is likewise fundamentally disadvantageous. The polymers in question thus form a ballast. This ballast is particularly undesirable in the use of washing or cleaning agents as it can lead to e.g. unwanted residues in the application and therefore to e.g. a functional or esthetic impairment. It is also possible that the polymers in question resist degradation, thereby running counter to the basic requirement of the greatest possible minimization of the environmental burden.

Based on this background, the object of the present invention was to overcome the cited disadvantages.

In addition, it is desirable to . . . . Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A washing or cleaning agent, comprising at least one hydrogelator with a molecular weight of less than 3500 g/mol, wherein the hydrogelator is water-soluble at concentrations below the minimum gelation concentration, wherein the minimum gelation concentration is that concentration, at which a yield stress of at least 0.05 Pa is formed in a binary solution of water and hydrogelator at T=25° C., and wherein this minimum gelation concentration is less than 2 wt % of hydrogelator, based on the system consisting of water and hydrogelator.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In the context of the present invention it was surprisingly found that the use of certain hydrogelators in washing or cleaning agents is very well applicable for the production of hydrogel layers on hard or textile surfaces. The use of at least two different low molecular weight hydrogelators and a multi-step method are thus not necessary for the production of the layers. In addition, there results no insoluble polymer ballast.

This is not known from the prior art. In U.S. Pat. No. 6,576,679 B2 there is described the formation of a hydrogel by the use of a cationic low molecular weight amphiphilic builder of the glutamine derivative type in the presence of certain anions. In EP 1 553 109 A1 is described a molecular-oriented polymer gel that is obtained by self-assembly of a self-organizable amphiphilic compound and a monomer interacting with the amphiphilic compound, and subsequent polymerization of the monomer. A class of substances of low molecular weight hydrogelators that are suitable for thickening or gelling solvents such as e.g. water is described in WO 03/097587. The production of hydrogel layers on surfaces from aqueous solutions is not described therein. Furthermore, numerous low molecular weight hydrogelators are cited in both of the following review articles: (a) Loos, Feringa, Esch, *Eur. J. Org. Chem.* 2005, 3615, (b) Estroff, Hamilton, *Chem. Rev.* 2004, 104, 1201. However, the use of corresponding hydrogelators in washing or cleaning agents for the production of hydrogel layers on surfaces from aqueous solution is not described.

On this basis, a first subject matter of the invention is a washing or cleaning agent that comprises at least one hydrogelator with a molecular weight of less than 3500 g/mol, wherein the hydrogelator is water-soluble at concentrations below the minimum gelation concentration,
wherein the minimum gelation concentration is that concentration, at which a yield stress of at least 0.05 Pa is formed in a binary solution of water and hydrogelator at T=25° C., and wherein this minimum gelation concentration is less than 2 wt % of hydrogelator, based on the system consisting of water and hydrogelator.

The yield stresses are measured with a rotational rheometer from TA Instruments, type AR G2. This is a controlled shear stress rheometer. Various methods for measuring a yield stress with a controlled shear stress rheometer are described in the literature and known to the person skilled in the art.

In the context of the present invention the yield stress was determined as follows:

In the rheometer the samples were subjected to a shear stress s(t) that increased with time. For example, the shear stress can be increased in the course of 10 minutes from the smallest possible value (e.g. 2 mPa) to e.g. 10 Pa. The deformation g of the sample is measured as a function of this shear stress. The deformation is plotted in a log-log plot against the shear stress. In so far as the sample has a yield stress, then two different regions clearly exist in this plot. Below a certain shear stress one finds a purely elastic deformation. The slope of the curve g(s) (log-log plot) in this region is one. The region of flow begins above this shear stress and the slope of the curve is dramatically higher. The shear stress at which the curve deviates, i.e. the transition from the elastic into a plastic deformation, marks the yield stress. The inflexion point can be conveniently determined by creating tangents on both parts of the curve. Samples without a yield stress do not exhibit a characteristic inflexion point in the function g(s).

A hydrogelator in the context of the invention is capable of self-organization when forming hydrogels. Gels as such have to contain at least two components, namely a liquid and a solid ingredient that forms a three-dimensional network that confines the liquid within it. In hydrogels in the context of the invention the solid ingredient forms a three-dimensional network that confines water or an aqueous solution within it.

In the context of the invention a hydrogelator is accordingly a compound that is capable of self-organization when forming a hydrogel.

The hydrogels according to the invention do not concern covalent gels, i.e. the network structure is the result of intermolecular or physical interactions (e.g. dipole-dipole forces, hydrogen bonding, aromatic π-π-interactions, van der Waals interactions, ionic interactions, ion-dipole interactions, cation-π-interactions or Coulomb forces) between the molecules and not the result of covalent bonds between the building blocks or molecules. The three-dimensional network structure can also result from non-specific entanglements or from contact between the building blocks, wherein these building blocks are then aggregates of smaller molecules that themselves are linked through non-covalent bonds e.g. to rods or chains. The formation of the hydrogels according to the invention is thus based on supramolecular interactions of the hydrogelator according to the invention. Hydrogels thus result by self-assembly.

The inventive formation of the hydrogels on the surfaces is additionally based on interactions of the hydrogelator according to the invention with the surface to be coated. In this way gel layers result on the surfaces already at concentrations in which still no gelation occurs in the solution (i.e. the minimum gelation concentration in the presence of the surface is smaller than the minimum gelation concentration in the solution), which is very advantageous. Here the minimum gelation concentration is the concentration of a hydrogelator in homogeneous aqueous solution, at or above which it forms a hydrogel, i.e. a network results from a self-organization process, water being entrapped in the network, thereby converting the liquid into a coherent gel. Therefore, the hydrogel layers can be produced without having to gelate or thicken the aqueous solution itself.

Low molecular weight hydrogelators are known from the literature, as has already been mentioned. Reference may be made here in particular to the already mentioned review articles and the hydrogelators cited therein: (a) Loos, Feringa, Esch, *Eur. J. Org. Chem.* 2005, 3615, (b) Estroff, Hamilton, *Chem. Rev.* 2004, 104, 1201. In principal in the context of the invention all hydrogelators known from the literature and especially the hydrogelators cited in the two mentioned review articles can be employed, in so far as they are water-soluble at concentrations below the minimum gelation concentration, wherein the minimum gelation concentration is that concentration, at which a yield stress of at least 0.05 Pa is formed in a binary solution of water and hydrogelator at T=25° C., and wherein this minimum gelation concentration is less than 2 wt % of hydrogelator, based on the system consisting of water and hydrogelator, and in so far as their molecular weight is less than 3500 g/mol.

When the molecular weight of the hydrogelator according to the invention is less than 3000 g/mol, preferably less than 2500 g/mol, more advantageously less than 2000 g/mol, especially less than 1500 g/mol, then this corresponds to a preferred embodiment of the invention.

Many of the known low molecular weight hydrogelators can be classified as amphiphiles. Amphiphiles contain a polar (hydrophilic) part and a non-polar (hydrophobic) part.

In the context of the present invention particularly preferred hydrogelators preferably satisfy the following basic Formula (I)

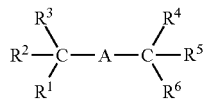

wherein the groups A, $R^1$ to $R^6$ have the following meaning:

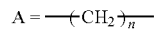

with n=1 to 24, preferably 6 to 18, in particular 8 to 14, or

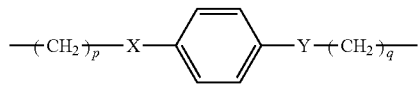

with p, q independently of one another=0 to 20, e.g. 1 to 16 with

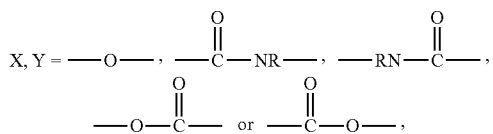

wherein X and Y can be selected independently of one another, and R is =H, alkyl or aryl, $R^1$ to $R^6$, each independently of one another: alkyl-, hydroxyalkyl-, aminoalkyl-, —COOR, —CONRR or

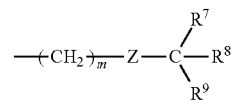

m = 0-10 in which Z=—CONH—$(CH_2)_r$—, —COO—$(CH_2)_r$—, —O—$(CH_2)_r$— or —CONR—$(CH_2)_r$— with r=0 to 10 and $R^7$ to $R^9$ independently of one another =H, alkyl, hydroxyalkyl, aminoalkyl, —CONRR, —COOR or monosaccharides,
wherein R=H, alkyl or aryl.

Quite particularly preferred inventively employable hydrogelators satisfy one of the following Formulas (II), (III), (IV) or (V):

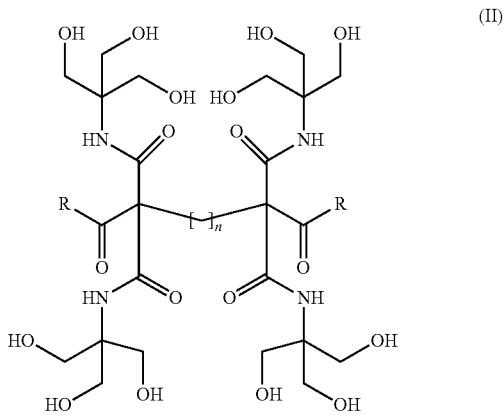

with n=1 to 24, preferably 6 to 18, in particular 8 to 14, e.g. 12, and R=HO—, alkyl-O— (such as especially $C_2H_5$—O—) or $(CH_2OH)_3C$—NH—.

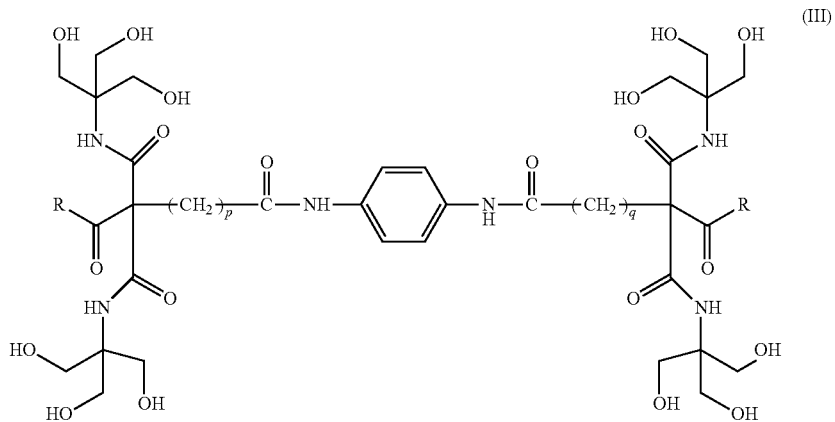
(III)
with p, q independently of one another=0 to 20, e.g. 1 to 16 and R=HO—, alkyl-O— (such as especially $C_2H_5$—O—) or $(CH_2OH)_3C$—NH—.
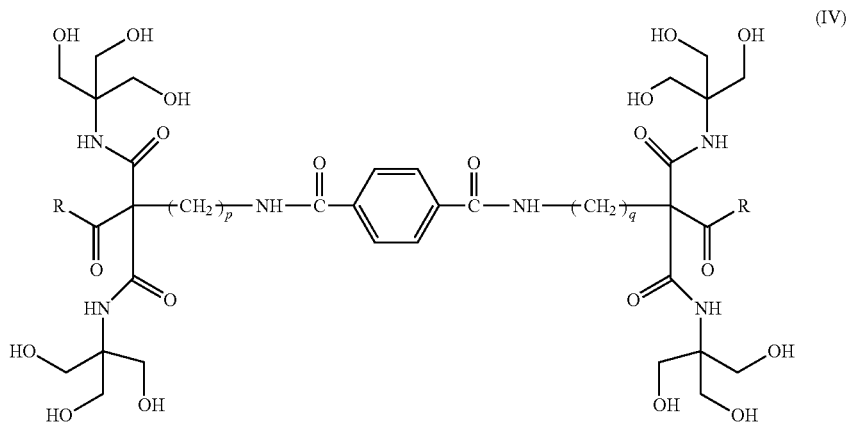
(IV)
with p, q independently of one another=0 to 20, e.g. 1 to 16 and R=HO—, alkyl-O— (such as especially $C_2H_5$—O—) or $(CH_2OH)_3C$—NH
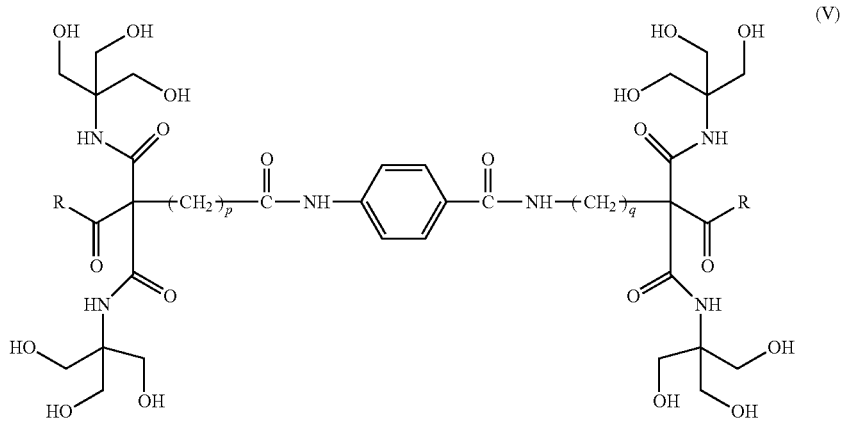
(V)

with p, q independently of one another=0 to 20, e.g. 1 to 16 and R=HO—, alkyl-O— (such as especially $C_2H_5$—O—) or $(CH_2OH)_3C$—NH—.

If at least one hydrogelator that satisfies one of the Formulas (II) to (V) is employed in the washing or cleaning agent according to the invention, then this constitutes a quite particularly preferred embodiment of the invention.

In the context of the present invention further particularly preferred hydrogelators preferably satisfy the following basic Formula (VI):

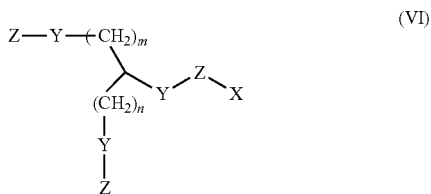

with n=0 to 10, m=0 to 24

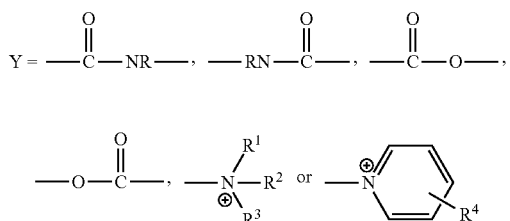

X=H, alkyl, aryl, alkylaryl ether,
  with halide, alkyl sulfonate, aryl sulfonate as the counter ion in the case of a cationic compound
Z=H, alkyl, aryl, alkylaryl ether
$R^1$ to $R^4$ independently of one another =H, alkyl, hydroxyalkyl or aryl
R=H, alkyl or aryl.

Particularly preferred representatives of this class of substances according to the basic Formula (VI) are the following:

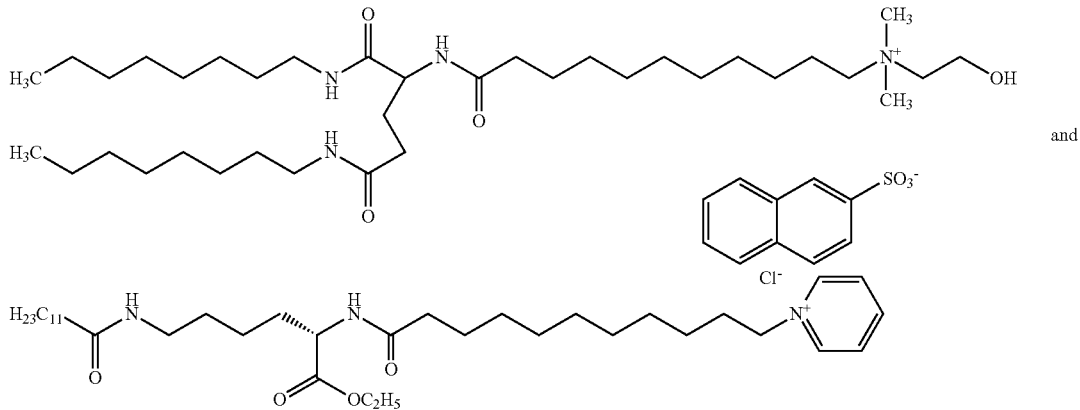

Here, other suitable anions can also serve as the anions.

The inventive subject matter enables the production of hydrogel layers on hard or textile surfaces (preferably induced by the surfaces) even in the presence of surfactants out of aqueous solution, in particular in relation to automatic washing or cleaning processes.

The inventive subject matter involves a series of advantages. For example it renders possible the hydrophilization of surfaces. This enables soils to be easily removed or washed off these surfaces (so-called soil release effect). Moreover, this lends an improved soil repellency to the surfaces, such that soiling of the surface is more difficult (the soil repellency effect).

Furthermore, with textiles the feel of the laundered products is positively influenced. Cotton-containing textiles in particular often show a hard feel when washed. In contrast, the textiles treated with the help of the washing or cleaning agent according to the invention exhibit a soft feel.

Another advantage is that as the layer is being formed, i.e. when hydrogel layers are produced on hard or soft (especially textile) surfaces, active substances can be deposited into the layers in or onto the layers, such that the layers can serve as a deposit or reservoir for active substances (such as e.g. perfumes, care substances, antimicrobials). In this regard the active substances can be dissolved in the liquid entrapped in the gel, they can be trapped inside the structures and/or be adsorbed on them. They can even be a constituent of the structures that make up the gel layer.

Consequently, the washing or cleaning agents according to the invention have the advantage that they enable a delayed release of active substances, especially fragrances and antimicrobials that are stored in the gel layers. When using the washing or cleaning agent, e.g. when washing textiles, it involves the formation of hydrogel layers on the item to be cleaned. In this way a controlled release of active substance is realized directly on the treated item, such that the performance profile of the agent as a whole is increased. In this regard, particular significance is attributed especially to the fragrance effect, as in many cases the consumer judges the product performance as a function of the pleasant odor. The release of the active substances, especially fragrances from the gel layer, can occur e.g. by diffusion, in which the active substances, especially fragrances, are released slowly and continuously. The present washing or cleaning agent thus enables a sustained and continuous release of active substances, in particular a sustained fragrancing of the item to be cleaned together with a controlled release of active substance directly on the target object. A particular advantage of the hydrogel layer according to the invention is that as the hydrogel layers dissolve they disintegrate again into their low molecular weight constituents, such that e.g. no poorly degradable polymers remain.

Still more particularly advantageous hydrogelators that can be employed in the context of this invention are cited below:

a) N,N'-bis(alkylamino)oxalamides, such as in particular

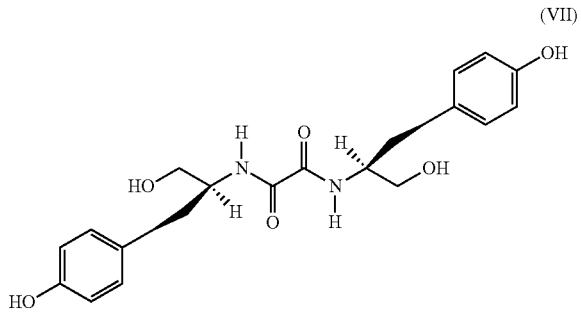
(VII)

b) Bis-urea dicarboxylic acid-based hydrogelators, such as in particular

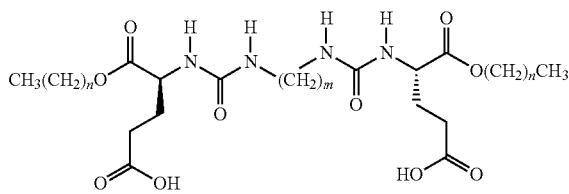
VIII with n=6 to 18 and m=1 to 18, e.g. with n=11 and m=8.

c) Lysine-based bis-amide-carboxylate, -pyridinium or -ammonium compounds, such as in particular

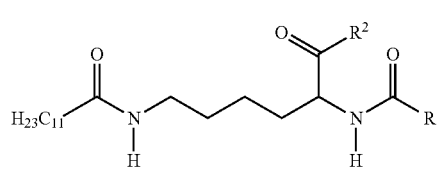
(IX)

with $R^1 = C_nH_{2n+1}$;

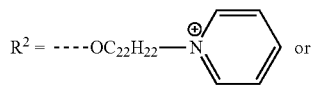

$R^2$ = ----$OC_{22}H_{22}$—N⊕  or with $R^1$ = ----$C_{10}H_{20}$—N⊕ ;

$R^2 = OC_2H_5/OC_{10}H_{21}$  or with $R^1 = C_{11}H_{23}$;  $R^2 = O^-Na^+$ with n = 1 to 20 or such as in particular

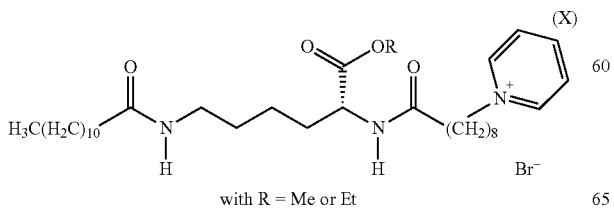
(X)

with R = Me or Et or such as in particular

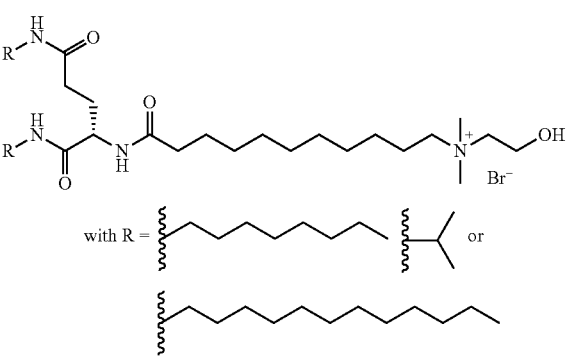
(XI)

d) Cyclohexane-1,2-bis-urea amides, such as in particular

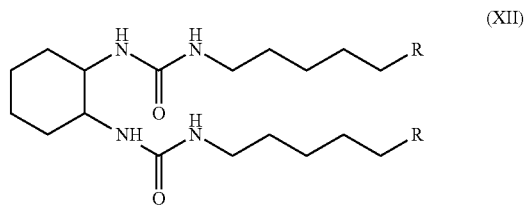
(XII)

with R = OH, CH$_2$OH or CH$_2$NH$_2$ e) cis-cis-1,3,5-Cyclohexane tris amino acid amides such as in particular

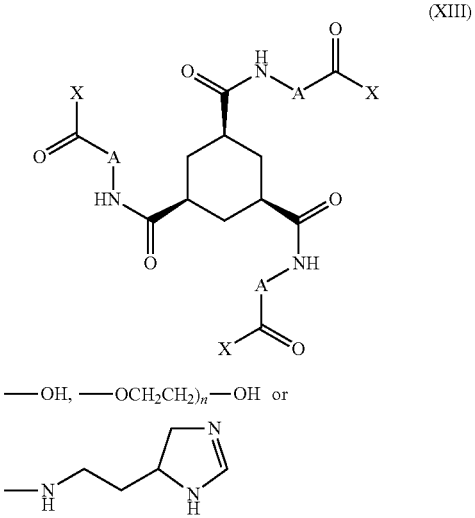
(XIII)

X = —OH, —OCH$_2$CH$_2$)$_n$—OH or

-continued

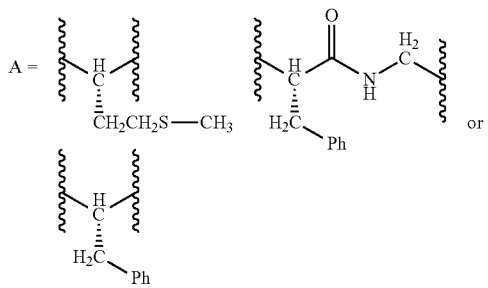

n = 1 to 10 f) N-Alkylaldonamides,
such as in particular N-dodecylgluconamide (XIV)

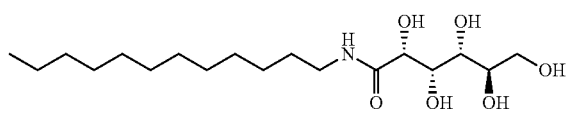

g) amino acid-based or serine-based hydrogelators
such as in particular N-dodecanoyl-(D- and L-)serine (XV)

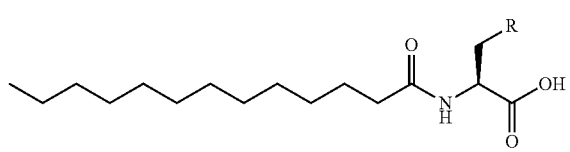

with R=—H, —OH, —CH$_2$—COOH oder —(CH$_2$)$_2$—COOH
or in particular (XVI)

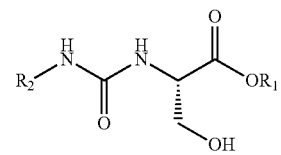

with R$_1$=H, alkyl or aryl
and with R$_2$=alkyl h) Bola-amphiphiles (this is the collective term for amphiphiles, whose hydrophobic group, generally hydrocarbon chains, is substituted in the α,ω-positions with two (hydrophilic, ionic and/or non-ionic) polar groups), such as especially sugar derivatives or amino acid-based Bola-amphiphiles:

(XVII)

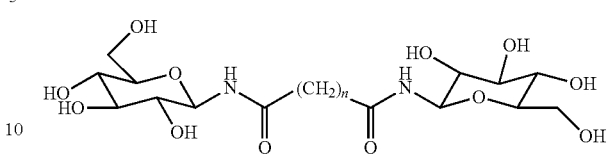

with n=6, 9, 10, 11, 12, 13 or 14,
or (XVIII)

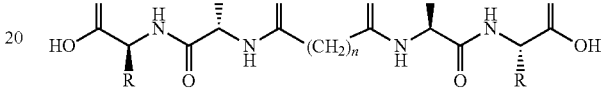

with n=8 or 10
with R=H, alkyl or aryl
or (XIX)

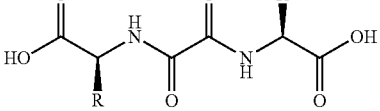

with n=5, 6 or 10
i) Bis-(amino acid) oxalyl amide with bulky (e.g. phenyl or isopropyl) side chains, such as in particular (XXI)

with R=alkyl or aryl e.g.

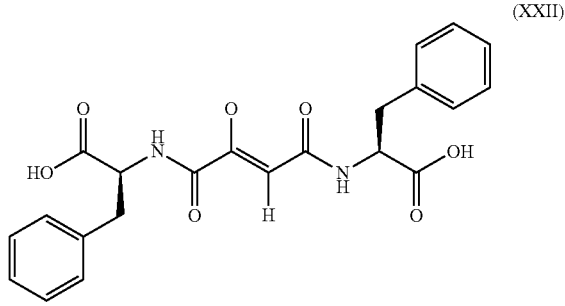 [SMILES: O=C(/C=C(\O)C(=O)N[C@@H](Cc1ccccc1)C(=O)O)N[C@@H](Cc1ccccc1)C(=O)O]

(XXII)

According to a preferred embodiment of the invention, the agent according to the invention comprises a total quantity of hydrogelator of 0.01 to 20 wt %, preferably 0.1 to 5 wt %, based on the total agent. In particular, within the cited concentration ranges, the use of the corresponding washing or cleaning agent allows the desired hydrogel layers to be particularly well produced on hard or soft surfaces.

The inventive washing or cleaning agent preferably comprises, in addition to the described hydrogelators, still further ingredients, namely in particular at least surfactants and/or builders. Surfactants are preferably comprised in quantities of 0.1 to 40 wt %.

Firstly, it should be made clear that the term "washing agent" in the context of this invention especially includes fabric washing agents as well as fabric post-treatment agents (such as preferably fabric softeners, fragrant rinses, conditioning cloths for use in laundry dryers, hygienic rinses etc.). Fabric washing agent is the name for the formulations required when washing fabrics, e.g. in the form of powders, granules, pearls, tablets, pastes, gels, cloths, pieces or liquids, which are employed preferably in aqueous solutions especially in washing machines. Fabric softeners are fabric post-treatment agents for fabric care and preferably comprise active principles that lend a soft feel to the treated fabrics, in particular cationic active principles (preferably cationic surfactants, e.g. quaternary ammonium compounds), fatty acid derivatives and/or silicone oils. Fragrant rinses are perfume-containing fabric post-treatment agents for fabric care and provide a particularly pleasant fragrance to the fabrics. Conditioning cloths for use in a laundry dryer are non-wovens or sheets that are impregnated with active principles (especially fabric softeners). Hygiene rinses are fabric post-treatment agents for fabric care and comprise at least one antimicrobial active principle, e.g. quaternary ammonium compounds such as e.g. benzalkonium chloride, and serve to reduce the germ count of the laundry.

The term "cleaning agent" includes all cleaners for hard or soft surfaces, but preferably hard surfaces, wherein especially dishwasher detergents (including hand dishwasher detergents and machine dishwasher detergents), all-purpose cleaners, WC-cleaners, sanitary cleaners as well as glass cleaners may be cited.

All washing or cleaning agents can be in the form of e.g. powders, granules, pearls, tablets, pastes, gels, cloths, pieces or liquids. They can be mono-phasic or multi-phasic. They can also be in single-dose packages, so-called pouches.

The washing or cleaning agents particularly preferably comprise at least surfactants and/or builders.

Anionic surfactants, non-ionic surfactants, cationic, zwitterionic and/or amphoteric surfactants are especially considered as the surfactants. However, the inventive washing or cleaning agent particularly preferably comprises anionic, non-ionic and/or cationic surfactants. The use of a mixture of anionic and non-ionic surfactants is particularly advantageous. The inventive washing or cleaning agent preferably comprises 0.05 to 50 wt %, more advantageously 1 to 40 wt %, still more advantageously 3 to 30 wt % and in particular 5 to 20 wt % surfactant(s), in particular from the group of the anionic surfactants, non-ionic surfactants, cationic, zwitterionic and/or amphoteric surfactants. This corresponds to a preferred embodiment of the invention and provides optimal cleaning powers.

Preferred employable surfactants are now described below and additionally in more detail further on.

It is particularly preferred, when the inventive washing or cleaning agent comprises anionic surfactant, advantageously in amounts of 0.1 to 25 wt %, more advantageously 1 to 20 wt %, in particular in amounts of 3 to 15 wt %, relative to the total agent. This corresponds to a preferred embodiment of the invention and provides particularly advantageous cleaning powers. A particularly suitable anionic surfactant is alkylbenzene sulfonate, preferably linear alkylbenzene sulfonate (LAS). If the inventive washing or cleaning agent comprises alkylbenzene sulfonate, advantageously in amounts of 0.1 to 25 wt %, more advantageously 1 to 20 wt %, in particular in amounts of 3 to 15 wt %, relative to the total agent, then this is a preferred embodiment of the invention.

Further particularly suitable anionic surfactants are the alkyl sulfates, in particular the fatty alcohol sulfates (FAS), such as e.g. $C_{12}$ to $C_{18}$ fatty alcohol sulfate. $C_8$-$C_{18}$ Alkyl sulfates can preferably be added, $C_{1-3}$ alkyl sulfate as well as $C_{13-15}$ alkyl sulfate and $C_{13-17}$ alkyl sulfate are particularly preferred, advantageously branched, especially alkyl-branched $C_{13-17}$ alkyl sulfate. Particularly suitable fatty alcohol sulfates are derived from lauryl alcohol and myristyl alcohol and are therefore fatty alcohol sulfates with 12 or 14 carbon atoms. If the inventive washing or cleaning agent comprises alkyl sulfate, in particular $C_{12}$ to $C_{18}$ fatty alcohol sulfate, advantageously in amounts of 0.1 to 25 wt %, more advantageously 1 to 20 wt %, in particular in amounts of 3 to 15 wt %, relative to the total agent, then this is a preferred embodiment of the invention.

Other preferred anionic surfactants that can be used are e.g. alkane sulfonates (e.g. secondary C13-C18 alkane sulfonate), methyl ester sulfonates (e.g. α-C12-C18 methyl ester sulfonate) and α-olefin sulfonates (e.g. α-C14-C18 olefin sulfonate) and alkyl ether sulfates (e.g. C12-C14 fatty alcohol-2EO-ether sulfate) and/or soaps. Further suitable anionic surfactants will be described further below. However, FAS and/or LAS are particularly suitable.

Particularly preferred anionic surfactants are soaps. Saturated and unsaturated fatty acid soaps are suitable, such as the salts of lauric acid, myristic acid, palmitic acid, stearic acid, (hydrogenated) erucic acid and behenic acid, and especially soap mixtures derived from natural fatty acids such as coconut oil fatty acid, palm kernel oil fatty acid, olive oil fatty acid or tallow fatty acid.

It is particularly preferred, when the inventive washing or cleaning agent comprises non-ionic surfactant, advantageously in amounts of 0.01 to 25 wt %, more advantageously 1 to 20 wt %, in particular in amounts of 3 to 15 wt %, relative to the total agent. This corresponds to a preferred embodiment of the invention. The use of alkyl polyglycol ethers is particularly preferred, in particular in combination with anionic surfactant, such as preferably LAS.

Further suitable non-ionic surfactants are alkylphenol polyglycol ethers (APEO), (ethoxylated) sorbitol fatty acid esters (sorbitanes), alkyl polyglucosides (APG), fatty acid glucamides, fatty acid ethoxylates, amine oxides, ethylene oxide-propylene oxide block polymers, polyglycerol fatty acid esters and/or fatty acid alkanolamides. Further suitable non-ionic surfactants will be described further below. Non-ionic surfactants based on sugars, such as especially APG, are particularly preferred.

In the context of the invention, the preferably employed builders include in particular polycarboxylates, citrates (e.g.

sodium citrate), soda, sodium hydrogen carbonate, phosphates, sodium silicates (water glass), phosphonates, zeolites, alkaline amorphous disilicates as well as crystalline layered silicates. The inventive washing or cleaning agent preferably comprises builders in amounts of 0.1 to 80 wt %, advantageously 1 to 60 wt %, more advantageously 5 to 60 wt %.

Furthermore, it is quite particularly preferred that the inventive washing or cleaning agent comprises a builder system (i.e. at least 2 substances having a builder effect), preferably a zeolite-containing builder system, preferably containing zeolite in amounts >1 wt %, more advantageously >5 wt %, further advantageously >10 wt %, especially ≥15 wt %, the wt % being relative to the total agent. A reasonable upper limit for zeolite can be e.g. 40 wt %, 30 wt % or 20 wt %, relative to the total agent. This corresponds to a preferred embodiment of the invention. A combination of zeolite with soda is preferred. The terms builder and builder substance are synonymous.

It is likewise particularly preferred if the inventive washing or cleaning agent comprises a soluble builder system, preferably containing soda, silicate, citrate and/or polycarboxylates, advantageously in amounts of 0.1 to 50 wt %, relative to the total agent. This corresponds to a preferred embodiment of the invention. If such a soluble builder system is comprised, then it is extremely preferred if only minor amounts of insoluble builder, such as in particular zeolite, are comprised, e.g. <5 wt % to 0.1 wt %; in such cases especially no insoluble builder is comprised at all.

It is likewise possible that the inventive washing or cleaning agent comprises phosphate, wherein phosphate is preferably comprised in amounts of 1 to 40 wt %, in particular 5 to 30 wt %, relative to the total agent. However, according to another preferred embodiment, the inventive washing or cleaning agent is free of phosphates.

The inventive washing or cleaning agents, which e.g. can be present in particular as powdery solids, in the form of post-compacted particles, as homogeneous solutions or suspensions, can in principle additionally comprise all known and customary ingredients for such agents. The inventive agents, as has already been shown, can comprise in particular builder substances, surfactants, also bleaching agents, bleach activators, water-miscible organic solvents, enzymes, sequestering agents, electrolytes, pH-regulators and additional auxiliaries, such as optical brighteners, fluorescent agents, anti-greying inhibitors, shrink preventers, anti-crease agents, color transfer inhibitors, antimicrobials, germicides, fungicides, antioxidants, preservatives, corrosion inhibitors, glass-corrosion inhibitors, disintegration auxiliaries, antistats, bittering agents, ironing aids, water repellents and impregnation agents, swelling and non-skid agents, neutral filling salts as well as UV-protection agents, foam regulators as well as dyes and fragrances.

Employable ingredients will be further described below to some extent.

According to a preferred embodiment of the invention, organic builders can be employed and can be comprised as required in amounts of e.g. up to 40 wt %, in particular up to 25 wt % and preferably from 1 to 8 wt %. Amounts close to the cited upper limit are preferably added in pasty or liquid, particularly aqueous, inventive agents.

In particular, crystalline or amorphous alkali metal aluminosilicates in amounts of up to 50 wt %, preferably not more than 40 wt % and in liquid agents not more than 1 to 5 wt % are added as the water-insoluble, water-dispersible inorganic builders. Among these, the washing agent-quality crystalline sodium alumosilicates, especially zeolite A, P and optionally X, alone or in mixtures, for example in the form of a co-crystallizate of the zeolites A and X (Vegobond® AX, a commercial product of Condea Augusta S.p.A.) are preferred. Amounts close to the cited upper limit are preferably incorporated in solid, particulate agents.

Suitable bleaching agents for use in the inventive washing or cleaning agents include for example peroxygen compounds such as in particular organic peracids or peracid salts of organic acids, such as phthalimidopercaproic acid, perbenzoic acid or salts of diperoxydodecanedioic acid, hydrogen peroxide and inorganic salts that liberate hydrogen peroxide under the washing conditions, such as perborate, percarbonate, persilicate and/or persulfate like Caroat. If it is intended to use solid peroxygen compounds, then they can be used in the form of powders or pellets, which in principle can also be encapsulated by known methods. When an inventive agent comprises peroxygen compounds then the latter are present in amounts of preferably up to 50 wt %, especially 5 to 30 wt %. The addition of minor quantities of known bleaching agent stabilizers, such as for example phosphonates, borates or metaborates and metasilicates as well as magnesium salts such as magnesium sulfate, can be useful.

Bleach activators, which can be employed, are compounds which, under perhydrolysis conditions, yield aliphatic peroxycarboxylic acids having preferably 1 to 10 carbon atoms, in particular 2 to 4 carbon atoms, and/or optionally substituted perbenzoic acid. Substances, which carry O-acyl and/or N-acyl groups of said number of carbon atoms and/or optionally substituted benzoyl groups, are suitable. Bleach activators, in particular in the presence of the abovementioned hydrogen peroxide releasing bleaching agents, can be comprised in the usual quantity range, preferably in amounts of 0.5 to 10 wt %, in particular 1 to 8 wt %, based on the total agent, but are preferably totally absent when percarboxylic acid is added as the sole bleaching agent.

Additionally employable enzymes in the inventive washing or cleaning agents can include those from the classes of the amylases, proteases, lipases, cutinases, pullulanases, hemicellulases, cellulases, oxidases, laccases, pectinases, carboanhydrases, mannanases, tannases and peroxidases as well as mixtures thereof.

Organic solvents that can be employed in addition to water in the inventive washing or cleaning agents, particularly when the agents are in liquid or paste form, include alcohols with 1 to 4 carbon atoms, particularly methanol, ethanol, isopropanol and tert-butanol, diols with 2 to 4 carbon atoms, particularly ethylene glycol and propylene glycol, as well as their mixtures and the ethers derived from the cited classes of compounds.

To adjust a pH resulting from mixing the usual components to a desired level, the washing or cleaning agents according to the invention can comprise acids that are compatible with the system and the environment, particularly citric acid, acetic acid, tartaric acid, malic acid, lactic acid, glycolic acid, succinic acid, glutaric acid and/or adipic acid, but also mineral acids, particularly sulfuric acid, or bases, particularly ammonium hydroxide or alkali metal hydroxides. These types of pH adjustors can optionally be comprised in the inventive agents in amounts of preferably not more than 20 wt %, particularly 1.2 to 17 wt %.

Particularly when used in automatic processes, it can be advantageous to add conventional foam inhibitors to the washing or cleaning agents. Suitable foam inhibitors include for example, soaps of natural or synthetic origin, which have a high content of $C_{18}$ to $C_{24}$ fatty acids. Suitable non-surface-active types of foam inhibitors are, for example, organopolysiloxanes and mixtures thereof with microfine, optionally silanized silica and also paraffins, waxes, microcrystalline waxes and mixtures thereof with silanized silica or bis-fatty acid alkylenediamides.

In order to enhance the aesthetic impression of the washing or cleaning agents, they may be colored with appropriate colorants. Preferred colorants, which are not difficult for the expert to choose, have high storage stability, are not affected by the other ingredients of the washing or cleaning agent and by light and do not have any pronounced substantivity for textile fibers, so as not to color them.

Suitable soil-release polymers, also referred to as antiredeposition agents, are for example non-ionic cellulose ethers such as methyl cellulose and methyl hydroxypropyl cellulose with a content of methoxy groups of 15 to 30 wt % and hydroxypropyl groups of 1 to 15 wt %, each based on the non-ionic cellulose ether, as well as polymers of phthalic acid and/or terephthalic acid or their derivatives known from the prior art, particularly polymers of ethylene terephthalates and/or polyethylene glycol terephthalates and/or polypropylene glycol terephthalates or anionically and/or non-ionically modified derivatives thereof. Suitable derivatives include the sulfonated derivatives of the phthalic acid polymers and the terephthalic acid polymers.

Optical brighteners (so called "whiteners") can be added to the washing or cleaning agents in order to eliminate graying and yellowing of the treated textile fabrics. These materials absorb onto the fiber and effect a brightening and pseudo bleach effect in that the invisible ultraviolet radiation is converted into visible radiation, wherein the ultraviolet light absorbed from sunlight is irradiated away as weak blue fluorescence and results in pure white for the yellow shade of the grayed or yellowed washing. Suitable compounds derive for example from the substance classes of the 4,4'-diamino-2,2'-stilbenedisulfonic acids (flavonic acids), 4,4'-distyrylbiphenylene, methyl umbelliferone, coumarone, dihydroquinolinones, 1,3-diarylpyrazolines, naphthoic acid imides, benzoxazole-, benzisoxazole- and benzimidazole-systems as well as the heterocyclic substituted pyrene derivatives. The optical brighteners are usually optionally added in amounts between 0% and 0.3 wt %, based on the finished agent.

Graying inhibitors have the function of maintaining the dirt that was removed from the fibers to be suspended in the washing liquor, thereby preventing the dirt from resettling. Water-soluble colloids of mostly organic nature are suitable for this, for example glue, gelatins, salts of ether sulfonic acids of starches or celluloses, or salts of acidic sulfuric acid esters of celluloses or starches. Water-soluble, acid group-containing polyamides are also suitable for this purpose. In addition, soluble starch preparations and others can be used as the abovementioned starch products, for example degraded starches, aldehyde starches etc. Polyvinyl pyrrolidone can also be used. Preference, however, is given to the use of cellulose ethers such as carboxymethyl cellulose (Na salt), methyl cellulose, hydroxyalkyl celluloses and mixed ethers such as methyl hydroxyethyl cellulose, methyl hydroxypropyl cellulose, methyl carboxymethyl cellulose and mixtures thereof, which can optionally be added in amounts of 0.1 to 5 wt %, based on the washing or cleaning agent.

In order to efficiently repress color dissolution and/or the color transfer to other textiles during washing and/or cleaning of colored fabrics, the washing or cleaning agent can comprise a color transfer inhibitor. The color transfer inhibitor is preferably a polymer or copolymer of cyclic amines such as for example vinyl pyrrolidone and/or vinylimidazole.

The amount of color transfer inhibitor based on the total weight of the washing or cleaning agent is preferably 0.01 to 2 wt %, advantageously from 0.05 to 1 wt % and more preferably from 0.1 to 0.5 wt %.

Because textile fabrics, particularly of rayon, spun rayon, cotton and their mixtures, tend to crease because the individual fibers are sensitive to flection, bending, pressing and squeezing at right angles to the fiber direction, the washing or cleaning agents can comprise synthetic anti-crease agents. They include for example synthetic products based on fatty acids, fatty acid esters, fatty acid amides, fatty acid alkylol esters, fatty acid alkylol amides or fatty alcohols that have mainly been treated with ethylene oxide, or products based on lecithin or modified phosphoric acid esters.

The washing or cleaning agents can comprise antimicrobial agents to control microorganisms. Depending on the antimicrobial spectrum and the action mechanism, antimicrobial agents are classified as bacteriostatic agents and bactericides, fungistatic agents and fungicides, etc. Important representatives of these groups are, for example, benzalkonium chlorides, alkylaryl sulfonates, halophenols and phenol mercuric acetate, wherein these compounds can also be totally dispensed with in the inventive washing or cleaning agents.

The inventive washing or cleaning agents can comprise preservatives, wherein preferably only those are used, which have no or only a slight skin sensitizing potential. Examples are sorbic acid and its salts, benzoic acid and its salts, salicylic acid and its salts, phenoxyethanol, 3-iodo-2-propynylbutyl carbamate, sodium N-(hydroxymethyl)glycinate, biphenyl-2-ol as well as mixtures thereof. A suitable preservative is illustrated by the solvent-free, aqueous combination of diazolidinyl urea, sodium benzoate and potassium sorbates (obtainable as Euxyle® K 500 ex Schuelke & Mayr), which can be employed in a pH range up to 7. In particular, preservatives based on organic acids and/or their salts are suitable for preserving the inventive skin-friendly washing or cleaning agents.

The washing or cleaning agents can comprise antioxidants in order to prevent undesirable changes caused by oxygen and other oxidative processes to the washing or cleaning agents and/or the treated textile fabrics. This class of compounds includes, for example, substituted phenols, hydroquinones, pyrocatechols and aromatic amines as well as organic sulfides, polysulfides, dithiocarbamates, phosphites, phosphonates and vitamin E.

An increased wear comfort can result from the additional use of antistats that can be additionally included in the washing or cleaning agents.

Finally, the washing or cleaning agents can also comprise UV absorbers that are absorbed on the treated textile fabrics and improve the light stability of the fibers.

Substances can be added to complex heavy metals in order to prevent heavy metal catalyzed decomposition of certain washing ingredients. Suitable heavy metal sequestrants are, for example, the alkali salts of ethylenediaminetetra acetic acid (EDTA) or of nitrilotriacetic acid (NTA) as well as alkali metal salts of anionic polyelectrolytes such as polymaleates and polysulfonates.

A preferred class of sequestrants are the phosphonates that are comprised in the preferred washing or cleaning agents in amounts of e.g. 0.01 to 2.5 wt %, preferably 0.02 to 2 wt % and particularly 0.03 to 1.5 wt %. These preferred compounds particularly include organophosphonates such as for example 1-hydroxyethane-1,1-diphosphonic acid (HEDP), aminotri (methylenephosphonic acid) (ATMP), diethylenetriamine penta(methylenephosphonic acid) (DTPMP or DETPMP) as well as 2-phosphonobutane-1,2,4-tricarboxylic acid (PBS-AM), which are mainly added in the form of their ammonium or alkali metal salts.

In addition, solid washing or cleaning agents can also comprise neutral filler salts such as sodium sulfate.

Liquid washing or cleaning agents can still further comprise e.g. thickeners, in order to adjust to a required viscosity. Suitable employable thickeners will also be described further below in connection with the fabric post-treatment agents. The thickeners cited there can also be employed in all other liquid washing or cleaning agents.

In particular, the washing or cleaning agents according to the invention can comprise perfume oils (fragrances). This corresponds to a particularly preferred embodiment of the invention. Based on the total washing or cleaning agent, preferably 0.0001 to 15 wt %, more advantageously 0.001 to 10 wt %, especially 0.01 to 5 wt % fragrances can be comprised therein.

As fragrances or perfumes or perfume oils, all substances and mixtures known as these can be used. In the context of this invention, the terms "perfume(s)", "fragrances" and "perfume oil(s)" are used synonymously. In particular, they mean any substances or their mixtures that are perceived by humans and animals as an odor, in particular by humans as a pleasant odor.

Perfumes, perfume oils or constituents of perfume oils can be employed as the fragrant components. Inventively, perfume oils or fragrances can be individual fragrant compounds, for example the synthetic products of the ester, ether, aldehyde, ketone, alcohol and hydrocarbon type.

A preferred powdered heavy duty detergent according to the invention can preferably comprise, in addition to the hydrogelators according to the invention, components that are selected from the following:

anionic surfactants, such as e.g. alkylbenzene sulfonate and/or alkyl sulfate, e.g. in amounts of preferably 0 to 40 wt %, advantageously 5 to 30 wt %, preferably 8 to 25 wt %, especially 10 to 20 wt %,
non-ionic surfactants; such as e.g. fatty alcohol polyglycol ethers, alkyl polyglucoside, fatty acid glucamide e.g. in amounts of 0 to 30 wt %, more advantageously 0.1 to 20 wt %, preferably 2 to 15 wt %, especially 6 to 11 wt %,
builders, such as e.g. zeolite, polycarboxylates and/or sodium citrate, in amounts of e.g. 0 to 70 wt %, more advantageously 5 to 60 wt %, preferably 10 to 55 wt %, in particular 15 to 40 wt %,
alkalies in amounts of e.g. 0 to 35 wt %, more advantageously 1 to 30 wt %, preferably 2 to 25 wt %, in particular 5 to 20 wt %,
bleaching agents, such as e.g. sodium perborate and/or sodium percarbonate, in amounts of e.g. 0 to 30 wt %, more advantageously 5 to 25 wt %, preferably 10 to 20 wt %,
corrosion Inhibitors, e.g. sodium silicate in amounts of e.g. 0 to 10 wt %, more advantageously 1 to 6 wt %, preferably 2 to 5 wt %, in particular 3 to 4 wt %,
stabilizers, e.g. phosphonates, advantageously 0 to 1 wt %,
foam inhibitors, e.g. soaps, silicon oils and/or paraffins, advantageously 0 to 4 wt %, preferably 0.2 to 3 wt %, in particular 0.5 to 1.5 wt %,
enzymes, e.g. proteases, amylases, cellulases and/or lipases, advantageously 0 to 2 wt %, preferably 0.2 to 1 wt %, in particular 0.3 to 0.8 wt %,
graying inhibitors, e.g. carboxymethyl cellulose, advantageously 0 to 1 wt %,
discoloration inhibitors, e.g. polyvinyl pyrrolidone derivative, in particular 0 to 2 wt %,
adjustment means, e.g. sodium sulfate, advantageously 0 to 20 wt %,
optical brighteners, e.g. stilbene derivatives, biphenyl derivatives, advantageously 0.1 to 0.4 wt %, especially 0.1 to 0.3 wt %,
fragrances,
water,
soap,
bleach activators,
cellulose derivatives,
soil repellents, each wt % based on the total agent.

A preferred liquid heavy duty detergent can preferably comprise, in addition to the hydrogelators according to the invention, components that are selected from the following:

anionic surfactants, such as e.g. alkylbenzene sulfonate and/or alkyl sulfate, e.g. in amounts of preferably 0 to 40 wt %, advantageously 5 to 40 wt %, preferably 8 to 30 wt %, especially 10 to 25 wt-%,
non-ionic surfactants, such as e.g. fatty alcohol polyglycol ethers, alkyl polyglucoside, fatty acid glucamide e.g. in amounts of 0 to 30 wt %, more advantageously 0.1 to 25 wt %, preferably 5 to 20 wt %, especially 10 to 15 wt-%,
builders, such as e.g. zeolite, polycarboxylate and/or sodium citrate, advantageously 0 to 15 wt %, preferably 0.01 to 10 wt %, in particular 0.1 to 5 wt %
foam inhibitors, e.g. soaps, silicon oils and/or paraffins, in amounts of e.g. 0 to 10 wt %, advantageously 0.1 to 4 wt %, preferably 0.2 to 2 wt %, in particular 1 to 3 wt,-%,
enzymes, e.g. proteases, amylases, cellulases and/or lipases, in amounts of e.g. 0 to 3 wt %, advantageously 0.1 to 2 wt %, preferably 0.2 to 1 wt %, in particular 0.3 to 0.8 wt %,-%,
optical brighteners, e.g. stilbene derivatives and/or biphenyl derivatives, in amounts of e.g. 0 to 1 wt %, advantageously 0.1 to 0.4 wt %, especially 0.1 to 0.3 wt-%,
fragrances,
stabilizers,
water,
soaps in amounts of e.g. 0 to 25 wt %, more advantageously 1 to 20 wt %, preferably 2 to 15 wt %, in particular 5 to 10 wt-%,
alcohols/solvents, advantageously 0 to 25 wt %, preferably 1 to 20 wt %, especially 2 to 15 wt %, each wt % based on the total agent.

Another subject matter of the invention is a method for washing fabrics by employing an inventive washing or cleaning agent (as described above), preferably in an automatic washing machine, wherein the wash temperature is ≤60° C., preferably ≤40° C.

Preferred inventive washing or cleaning agents are fabric post-treatment agents. This is preferably a fabric softener, i.e. fabric post-treatment agents that comprise a softening component. Preferred active substances that are comprised in the fabric softener formulations according to the invention are cationic surfactants, especially esterquats. Esterquats are quaternary ammonium compounds with preferably two hydrophobic groups that each comprise an ester group as the so-called predetermined breakage point for an easier biodegradation.

If the fabric post-treatment agent according to the invention thus comprises a softening compound, wherein the amount of softening compound is preferably 2 to 80 wt %, advantageously 4 to 40 wt %, more preferably 6 to 20 wt % and especially 8 to 15 wt %, each based on the total agent, then this is a preferred embodiment of the invention. If a cationic surfactant is comprised, advantageously a quaternary ammonium compound, in particular an esterquat, preferably in amounts of >0.1 wt %, advantageously 1 to 40 wt %, especially 3 to 30 wt %, based on the total agent, then this is another preferred embodiment of the invention Post-treatment agents are usually brought into contact with the fabrics in the last step of a conventional fabric washing method, the rinsing step. The post-treatment can also occur in the washer-dryer, in particular by employing the previously mentioned drying cloths.

The softening component includes for example quaternary ammonium compounds such as monoalk(en)yltrimethylammonium compounds, dialk(en)yldimethylammonium compounds, mono-, di- or triesters of fatty acids with alkanolamines.

Alkylated quaternary ammonium compounds having at least one alkyl chain interrupted by an ester group and/or an amido group are particularly preferred softening components. N-Methyl-N-(2-hydroxyethyl)-N,N-(ditallowacyloxyethyl)ammonium methosulfate or bis-(palmitoyloxyethyl)hydroxyethylmethylammonium methosulfate are quite particularly preferred.

Quaternized protein hydrolyzates or protonated amines represent further inventively usable softening components.

In addition, cationic polymers are also suitable softening components. Suitable cationic polymers include the polyquaternium polymers such as those in the CTFA Cosmetic Ingredient Dictionary (The Cosmetic, Toiletry and Fragrance, Inc., 1997), particularly those polyquaternium-6, polyquaternium-7, polyquaternium-10 polymers also described as Merquats (Polymer JR, LR and KG series from Amerchol), polyquaternium-4-copolymers, such as graft copolymers with a cellulosic backbone and quaternary ammonium groups that are bonded through allyldimethylammonium chloride, cationic cellulose derivatives like cationic guar, such as guarhydroxypropyltriammonium chloride, and similar quaternized guar derivatives (e.g. Cosmedia Guar, manufactured by Cognis or the Jaguar series from Rhodia), cationic quaternary sugar derivatives (cationic alkyl polyglucosides), e.g. the commercial product Glucquat® 100, according to CTFA nomenclature a "Lauryl Methyl Gluceth-10 Hydroxypropyl Dimonium Chloride", copolymers of PVP and dimethylamino methacrylate, copolymers of vinyl imidazole and vinyl pyrrolidone, amino silicone polymers and copolymers.

Polyquaternized polymers (e.g. Luviquat® Care from BASF) and also cationic biopolymers based on chitin and its derivatives, for example the polymer obtained under the trade name Chitosan® (manufacturer: Cognis) can also be employed.

Further suitable softening components include protonated or quaternized polyamines.

The fabric post-treatment agent, as also the totality of the washing or cleaning agent, can additionally comprise at least one aromatherapy component. Preferably, an ethereal oil can be employed as the aromatherapy component. Ethereal oils also fall under the umbrella term of the fragrances.

The amount of ethereal oil in the washing or cleaning agent, preferably fabric post-treatment agent, is preferably 0.0001 to 3 wt %, especially preferably 0.01 to 1 wt % and quite particularly preferably 0.05 to 0.5 wt %.

A preferred fabric post-treatment agent according to the invention contains, in addition to the hydrogelators according to the invention, especially
  a) softening compound, advantageously cationic surfactants, preferably esterquats, advantageously in amounts of 5 to 30 wt %, e.g. 10 to 20 wt-%,
  b) surfactants, preferably non-ionic surfactants, e.g. fatty alcohol ethoxylates, advantageously in amounts of 0 to 5 wt %, e.g. 0.1 to 3 wt-%.
  c) preservatives, advantageously in amounts of 0 to 2 wt %, e.g. 0.001 to 0.5 wt %,
  d) fragrances, advantageously in amounts of 0 to 10 wt % or 0 to 5 wt %, e.g. 0.01 to 1 wt %,
  e) colorants, advantageously in amounts of 0 to 0.1 wt %, e.g. 0.01 to 0.005 wt %,
  f) optionally water, preferably in amounts ≥50 wt % or ≥60 wt %, e.g. 70 to 95 wt % or e.g. 75 to 90 wt %,
  g) optionally solvents, preferably monohydric alcohols, especially 2-propanol, advantageously in amounts of 0.05 to 5 wt %, especially 0.1 to 4 wt %, in particular 0.3 to 3 wt %,
  h) optionally pH adjustors, preferably 0.01 to 5 wt %, in particular 0.02 to 1 wt %,
  i) optionally electrolytes, preferably from the group of inorganic salts, advantageously $MgCl_2$ or NaCl, 0.01 to 5 wt %, in particular 0.05 to 2 wt %,
  j) optionally skin-care active substances, such as e.g. almond oil, preferably in an amount of 0 to 15 wt %, e.g. 0.1 to 10 wt %, in particular 0.5 to 5 wt %,
  k) optionally thickeners, e.g. based on polyacrylate, preferably in amounts of 0.01 to 3 wt %, in particular 0.1 to 1 wt %,
each wt % based on the total agent.

Another subject matter of the invention is a fabric conditioning method using an inventive fabric post-treatment agent in the rinse cycle of an automatic washing machine.

Another subject matter of the invention is a fabric drying method using an inventive washing or cleaning agent in an automatic laundry dryer.

Another subject matter of the invention is a fabric conditioning method using an inventive fabric post-treatment agent in the form of a conditioning substrate in an automatic laundry dryer.

Another subject matter of the invention is in the use of an inventive fabric post-treatment agent for conditioning textile fabrics.

In the context of the invention, preferred agents are also the cleaning agents, especially cleaners for hard surfaces.

When the inventive cleaning agent is selected from the group of the hand dishwasher detergents, the machine dishwasher detergents, the toilet cleaners or WC-cleaners, the pipe cleaning agents or drain cleaners, the universal or all-purpose cleaners, the sanitary cleaners, the oven cleaners or grill cleaners, the metal polishes, the glass cleaners or window cleaners, the cleaning auxiliaries, the floor cleaners and the special cleaning agents, then there exists a preferred embodiment of the invention.

An advantage of the invention in connection with the cleaning agents is that of also providing a retarded and/or controlled release of active substances, such as e.g. fragrances, from the formed gel layers. In this way a frequently desired "slow release" effect or "long-lasting" effect and/or an accurate release of active principle directly on the treated object is provided. The cleaned surface, e.g. a floor, is uniformly fragrant for a long time or fragrances are released when the enclosed fragrances are given off. Similarly, other active substances, such as e.g. liquids with antimicrobial active principles, germicides, fungicides or other active principles can also be subjected to a retarded and/or controlled release.

In a preferred embodiment of the invention, a washing or cleaning agent according to the invention, in particular a cleaning agent, comprises an anionic polymer, advantageously in amounts of 0.2 to 30 wt %, preferably 0.5 to 20 wt % and especially 1 to 12 wt %, wt % based on the total agent.

When a copolymer, containing
i) unsaturated carboxylic acid(s)
ii) monomer(s) containing sulfonic acid groups
iii) additional non-ionic monomer(s)
is comprised as the anionic polymer, then once again a preferred embodiment of the invention exists.

If the washing or cleaning agent according to the invention, in particular a cleaning agent, comprises phosphonate, preferably selected from
  a) aminotrimethylene phosphonic acid (ATMP) and/or its salts;
  b) ethylenediaminetetra(methylene phosphonic acid) (EDTMP) and/or its salts;
  c) diethylenetriaminepenta(methylene phosphonic acid) (DTMP) and/or its salts;
  d) 1-hydroxyethane-1,1-diphosphonic acid (HEDP) and/or its salts;
  e) 2-phosphonobutane-1,2,4-tricarboxylic acid (PBTC) and/or its salts;
  f) hexamethylenediaminetetra(methylene phosphonic acid) (HDTMP) and/or its salts;
  g) nitrilotri(methylene phosphonic acid) (NTMP) and/or its salts,
then this a further preferred embodiment of the invention.

Cleaning agents in particular can comprise glass corrosion inhibitors. Glass corrosion inhibitors prevent the occurrence of smears, streaks and scratches as well as iridescence on the surfaces of glasses washed in an automatic dishwasher. Preferred glass corrosion inhibitors come from the group of the magnesium salts and zinc salts and magnesium complexes and zinc complexes.

A particular advantageous glass corrosion inhibitor is at least one zinc salt of an organic carboxylic acid, particularly preferably a zinc salt from the group zinc stearate, zinc oleate, zinc gluconate, zinc acetate, zinc lactate and/or zinc citrate. Zinc ricinoleate, zinc abietate and zinc oxalate are also preferred.

In the context of the present invention, the optimum content of zinc salt in the cleaning compositions is preferably between 0.1 and 5 wt %, preferably between 0.2 and 4 wt % and especially between 0.4 and 3 wt %, or the content of zinc in the oxidized form (calculated as $Zn^{2+}$) between 0.01 and 1 wt %, preferably between 0.02 and 0.5 wt % and especially between 0.04 and 0.2 wt % respectively, based on the total weight of the composition containing the glass corrosion inhibitor.

Another subject matter of the present application is a method for cleaning tableware in an automatic dishwasher, wherein the agent according to the invention is metered into the interior of an automatic dishwasher during the course of a dishwashing program, prior to the start of the main wash cycle or in the course of the main wash cycle. The inventive agent can be manually dispensed or metered into the interior of the automatic dishwasher, but the agent is preferably metered into the interior of the automatic dishwasher by means of the metering chamber.

Inventively preferred hand washing dishwasher agents can comprise, in addition to the hydrogelators according to the invention, for example:
a) surfactants, e.g. alkane sulfonates, alkyl ether sulfates, alkyl polyglucosides and/or cocoamido propyl betaine, preferably in amounts of 5 to 45 wt %, especially 10 to 40 wt %,-%,
b) optionally acidifiers, such as e.g. citric acid for adjusting the pH,
c) hydrotropes, such as e.g. cumene sulfonate, preferably in amounts from 0 to 15 wt %, especially 0.01 to 10 wt %,
d) refatting agents, such as e.g. fatty acid amides, preferably in amounts of 0 to 3 wt %, especially 0.01 to 3 wt %,
e) care components, such as e.g. aloe vera extracts, preferably in amounts of 0 to <5 wt %, especially 0.001 to <3 wt %,
f) fragrances, preferably in amounts of 0 to 3 wt %, especially 0.01 to 2 wt %,
g) optionally colorants,
h) antibacterial active substances, such as e.g. sodium benzoate or sodium salicylate, preferably in amounts of 0 to 3 wt %, especially 0.001 to 2 wt %,
i) preservatives, preferably in amounts of 0 to 1 wt %, especially 0.001 to 0.5 wt %.

In addition to the hydrogelators according to the invention, inventively preferred automatic dishwasher detergents can comprise e.g. sodium phosphates, preferably pentasodium phosphate, phosphonates, citrates, preferably sodium citrate, polycarboxylates, sodium metasilicates, soda, sodium hydrogen carbonate, sodium disilicate, active chlorine, sodium perborate, bleach activator TAED, enzymes, preferably protease and amylase, low-foaming non-ionic surfactants, silver/glass protectants as well as fragrances. Preferred automatic dishwasher detergents can be e.g. phosphate-based and highly alkaline or even e.g. phosphate-based and weakly alkaline. Other preferred automatic dishwasher detergents can be e.g. phosphate-free and weakly alkaline.

Another subject matter of the invention is a method for cleaning hard surfaces by employing a cleaning agent according to the invention, such as previously described, in combination with water.

Another subject matter of the invention is the use of hydrogelators according to the invention in washing or cleaning agents for the production of hydro gel layers on hard or fabric surfaces (initiated by the surfaces).

Another subject matter of the invention is a method for producing hydrogel layers on surfaces, especially hard or soft surfaces, wherein the surface in question is treated with a washing or cleaning agent according to the invention or with a liquid that contains a hydrogelator according to the invention.

This corresponds to a preferred embodiment of the invention when active substances, such as in particular fragrances, care substances, antimicrobials are attached into the layers in or on the layers in the course of the layer formation.

When the method according to the invention is provided for (a) rendering hard or soft surfaces hydrophilic, (b) facilitating the removability of soil from hard or soft surfaces, (c) improving the soil repellent capability of hard or soft surfaces, (d) retarded release of active substances, especially fragrances and antimicrobials that are sequestered in the gel layers, and/or (e) improving the soft feel of fabrics, then this constitutes a preferred embodiment of the invention.

When the method according to the invention is carried out in an automatic washing machine, preferably at temperatures ≤40° C., especially ≤30° C., then this constitutes a preferred embodiment of the invention.

Another subject matter of the invention is a method for washing fabrics that is carried out using a washing agent according to the invention. The method is preferably carried out in an automatic washing machine, preferably at temperatures ≤40° C., especially ≤30° C.

Another subject matter of the invention is a method for cleaning hard surfaces that is carried out using a cleaning agent according to the invention.

EXAMPLES

1. Synthetic Example

The following hydrogelator according to the invention (N1,N'1,N14,N'14-tetrakis[2-hydroxy-1,1-bis(hydroxymethyl)ethyl]-(1,1,1,14,14,14-tetradecanedicarboxyethyltetracarboxamide) was synthesized:

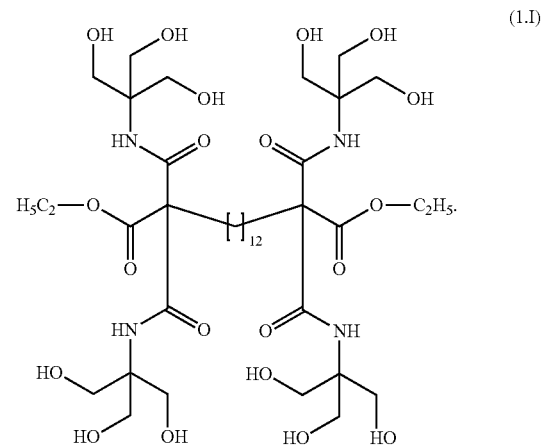

(1.I)

1,12-Dibromododecane (1 eq.) and triethyl methanetricarboxylate (2 eq.) were refluxed for 24 hours in toluene and DMF under an argon atmosphere with stirring. The reaction mixture was washed with water and a solution of $NaHCO_3$. The organic phase was dried and concentrated. The resulting product was dissolved in DMSO, and $Na_2CO_3$ (7 eq.) was added. Tris(hydroxymethyl)aminomethane (6 eq.) was dissolved in DMSO and added to the mixture. The batch was stirred at 80° C. The solvent was then removed. The crude product was purified with water and acetone.

Hydrolysis of the esters afforded the following compound:

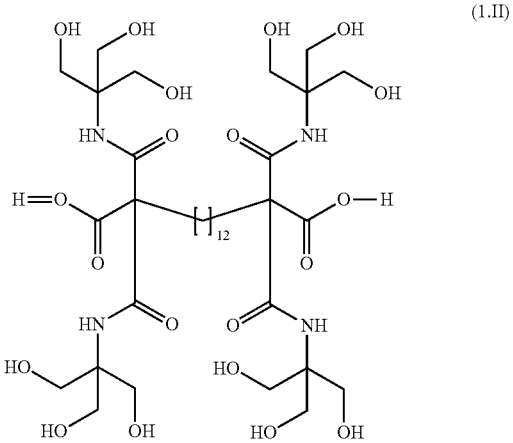

2. Examples of Usage 2.1.

An aqueous solution (0.05 wt %) of the hydrogelator according to the invention from the synthetic example (1.) described above was made up with water. A 25 mm×50 mm strip of material (polyester; grammage 130 g/m²) was dipped into this low viscosity solution, removed again and dried. The fabric was then examined by means of scanning electron microscopy. In comparison to the untreated fabric, a gel made up of gel fibrils was clearly observed on the treated fabric.

2.2.

An aqueous solution was produced comprising the hydrogelator according to the invention (0.05 wt %) from the synthetic example (1.) described above, a linear alkylbenzene sulfonate (0.044 wt %), Dehydrol LT 7 (0.044 wt %) (Dehydrol LT 7=C12-18 fatty alcohol, ethoxylated with 7 EO) and phenylethanol (0.1 wt %). An aqueous solution comprising linear alkylbenzene sulfonate (0.044 wt %), Dehydrol LT 7 (0.044 wt %) and phenylethanol (0.1 wt %) was prepared as a reference solution. A 25 mm×50 mm strip of material (polyester; grammage 130 g/m²) was dipped into each solution, removed again, dried and olfactorily assessed by trained olfactory experts. Already after 30 minutes phenylethanol could no longer be perceived on the polyester strip that had been dipped into the reference solution. After 4 hours phenylethanol could still be clearly perceived on the polyester strip that had been dipped into the solution comprising the hydrogelator according to the invention from the synthetic example (1.) mentioned above.

2.3. Use on WC Ceramics

A 0.1 wt conc. aqueous solution of the hydrogelator according to the invention from the synthetic example (1.) mentioned above was tested on WC ceramics against untreated WC ceramics.

Procedure:

WC ceramics from the Villeroy & Boch Company were subjected to a typical cleaning method and dried overnight in air.

The WC ceramics were uniformly sprayed using a trigger attachment with a 0.1 wt % conc. aqueous solution of the hydrogelator according to the invention from the synthetic example (1.) mentioned above and left to dry overnight.

In order to test the rinsing characteristics, 0.1 ml of an artificial fecal soil were deposited onto defined locations onto the WC ceramic, flushed with a defined amount of cold tap water, and the removal of the soil was evaluated according to the scale listed below.

The assessment was as follows:
0=no removal of the soil
1=ca. ¼ of the soil is removed
2=ca. half of the soil is removed
3=only minimum residues of the soil are still present
4=all the soil has been removed Average values from 14 WC ceramics and 42 measured locations

| Number of flushes | 1 | 2 | 3 | 4 | 5 |
|---|---|---|---|---|---|
| untreated samples | 0.5 | 1.1 | 1.1 | 2.0 | 2.3 |
| Samples treated with 0.1 wt % conc. aqueous solution of the inventive hydrogelator from synthetic example (1) | 1.0 | 1.9 | 2.2 | 2.4 | 2.7 |

With the ceramic treated with a 0.1 wt % conc. aqueous solution of the hydrogelator according to the invention from the synthetic example (1.) mentioned above there results an improved soil removal for the same number of rinses.

3. Product Examples

Example 3.1: Liquid Conditioner

|  | wt % |
|---|---|
| Esterquat[a] | 22.5 |
| Silicone oil | 5 |
| MgCl × 6H$_2$O | 0.5 |
| Perfume | 1.6 |
| Hydrogelator[c] | 0.5 |
| Water, deionized | ad 100 |

[a]N-Methyl-N(2-hdroxyethyl)-N,N-(ditallowacyloxyethyl)ammonium methosulfate
[c]Hydrogelator according to the invention from synthetic example (1.)

The formulation was produced by melting the esterquat in water. The molten esterquat was then stirred with a high dispersion device and the remaining components were added. After the mixture was cooled down to below 30° C., the perfume and the hydrogelator were added with light stirring.

Example 3.2 Conditioner Substrate

In order to produce the conditioner substrate, cellulose non-wovens (surface: 24.5×39 cm) were impregnated with 20 g of the liquid conditioner of Example 3.1.

Example 3.3 Liquid Cleaning Agent

| Raw material | Amount in wt % |
|---|---|
| C12-18 fatty acid, Na salt | 0.7 |
| C10-13 alkylbenzene sulfonate | 6.4 |
| Sodium citrate | 1.5 |
| Sodium carbonate | 3.0 |
| ethanol | 2.1 |
| Cumene sulfate, Na | 1.5 |
| C12-18 fatty alcohol + 7EO | 1.5 |
| C8 fatty alcohol sulfate, Na salt | 1.5 |
| Hydrogelator[c] | 0.5 |
| Perfume | 0.7 |
| Water | ad 100 |

[c]Hydrogelator according to the invention from synthetic example (1.)

Example 3.4 Liquid Washing Agent

| Raw material | Amount in wt % |
|---|---|
| C12-14 fatty acid | 8.8 |
| C12-18 fatty alcohol + 7EO | 24.0 |
| Alkyl polyglucoside | 2.0 |
| C12-14 2EO sulfate | 5.0 |
| C16-18 fatty acid | 6.8 |
| NaOH 50% | 3.0 |

-continued

| Raw material | Amount in wt % |
| --- | --- |
| Citric acid x 1H$_2$O | 1.0 |
| Glycerin 99.5% | 7.5 |
| Ethanol | 1.0 |
| Silicone oil | 0.3 |
| Polyvinyl pyrrolidone | 0.5 |
| HEDP-4Na | 0.5 |
| Enzyme, colorant, perfume | 0.8 |
| Hydrogelator[c] | 0.7 |
| Water | ad 100 |

[c]Hydrogelator according to the invention from synthetic example (1.)

Example 3.5 Solid Washing Agent

| Raw material | Amount in wt % |
| --- | --- |
| Alkylbenzene sulfonate (sodium salt) | 12 |
| Carboxymethyl cellulose | 1 |
| Enzymes | 1 |
| Non-ionic Surfactant | 3 |
| (1-Hydroxyethylidene)bisphosphonate | 1 |
| Sodium carbonate | 25 |
| Sodium percarbonate | 12 |
| sodium sulfate | 27 |
| Polyacrylate | 3 |
| Foam inhibitor | 2 |
| N,N,N',N'-Tetraacetylethylenediamine | 3 |
| Water | 3 |
| Perfume | 0.15 |
| Hydrogelator[C] | 1.0 |
| Sodium silicate | ad 100 |
| Total | 100 |

[C]Hydrogelator according to the invention from synthetic example (1.1.) sodium silicate: amorphous sodium silicate with Na$_2$O:SiO$_2$ = 2.4 Polyacrylate:polyacrylic acid, sodium salt; M = 4500 g/mol Example 3.6 Washing Agent Gel

| Raw material | Amount in wt % |
| --- | --- |
| Alkyl polyglucoside | 2.00 |
| C12-14 soap, Na | 8.80 |
| C16-18 soap, Na | 6.80 |
| NaOH 50% | 3.00 |
| Citric acid x 1H$_2$O | 1.00 |
| Glycerin 99.5% | 7.50 |
| Ethanol | 1.00 |
| Silicone defoamer | 0.30 |
| Boric acid | 1.00 |
| 1-Hydroxyethylenediphosphonic acid | 0.50 |
| Vinylimidazole-vinyl pyrrolidone copolymer | 1.67 |
| Perfume | 1.30 |
| Hydrogelator[c] | 0.80 |
| Water | ad 100 |

[c]Hydrogelator according to the invention from synthetic example (1.)

Example 3.7 Ironing Spray

| Raw material | Amount in wt % |
| --- | --- |
| Ethanol | 2 |
| Hydrogen peroxide | 0.01 |
| Perfume | 0.05 |
| Hydrogelator[c] | 0.02 |
| Water with 5° dH | ad 100 wt % |

[c]Hydrogelator according to the invention from synthetic example (1.)

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A washing or cleaning agent, comprising at least one hydrogelator with a molecular weight of less than 3500 g/mol, wherein the hydrogelator is water-soluble at concentrations below the minimum gelation concentration, wherein the minimum gelation concentration is that concentration, at which a yield stress of at least 0.05 Pa is formed in a binary solution of water and hydrogelator at T=25° C., and wherein this minimum gelation concentration is less than 2 wt % of hydrogelator, based on the system consisting of water and hydrogelator; and wherein the hydrogelator satisfies the following Formula (II):

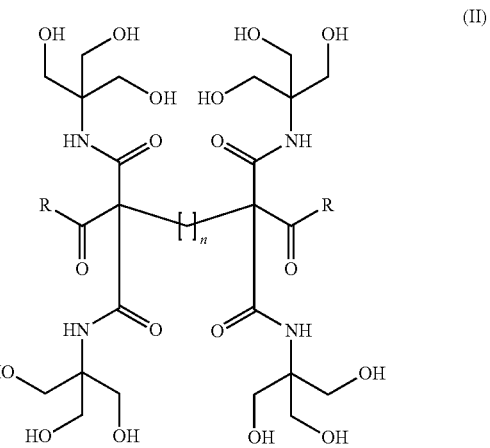

with n=1 to 24,
and R=HO—, alkyl-O— or (CH$_2$OH)$_3$C—NH—.

2. The agent according to claim 1, wherein the hydrogelator is comprised in amounts of 0.01 to 20 wt % based on the total agent.

3. The agent according to claim 1, comprising 0.1 to 40 wt % surfactant(s).

4. A method for the production of hydrogel layers on surfaces, wherein the surface is treated with a washing or cleaning agent according to claim 1.

5. The method according to claim 4, wherein fragrances are deposited during the layer formation into the layers or onto the layers.

6. The method according to claim 4, wherein it is carried out in an automatic washing machine at temperatures of ≤40° C.

7. The method according to claim 4, wherein nurturing ingredients are deposited during the layer formation into the layers or onto the layers.

8. The method according to claim 4, wherein antimicrobials are deposited during the layer formation into the layers or onto the layers.

* * * * *